United States Patent [19]
Pfeffer et al.

[11] Patent Number: 5,972,990
[45] Date of Patent: Oct. 26, 1999

[54] METHODS FOR REDUCING RISK OF REPEAT MYOCARDIAL INFARCTION AND INCREASING SURVIVAL IN HEART ATTACK VICTIMS

[75] Inventors: Marc A. Pfeffer; Janice M. Pfeffer, both of Chestnut Hill; Eugene Braunwald, Weston, all of Mass.

[73] Assignee: Brigham and Women's Hospital, Inc., Boston, Mass.

[21] Appl. No.: 07/981,196

[22] Filed: Nov. 25, 1992

Related U.S. Application Data

[63] Continuation-in-part of application No. 07/866,827, Apr. 10, 1992.

[51] Int. Cl.$^6$ .......................... A61K 38/00; A61K 31/40; A61K 31/535
[52] U.S. Cl. ..................... 514/423; 514/424; 514/236.2; 514/326; 514/340; 514/256; 514/259; 514/279; 514/381; 514/255; 514/616; 514/364; 514/16
[58] Field of Search ..................................... 514/381, 423, 514/424, 236.2, 326, 340, 361, 364, 200, 616

[56] References Cited

U.S. PATENT DOCUMENTS

| | | |
|---|---|---|
| 4,105,776 | 8/1978 | Ondetti et al. . |
| 4,302,386 | 11/1981 | Stevens . |
| 4,316,906 | 2/1982 | Ondetti et al. . |
| 4,337,201 | 6/1982 | Petrillo, Jr. . |
| 4,344,949 | 8/1982 | Hoefle et al. . |
| 4,374,829 | 2/1983 | Harris et al. . |
| 4,410,520 | 10/1983 | Watthey . |
| 4,508,729 | 4/1985 | Vincent et al. . |
| 4,512,924 | 4/1985 | Attwood et al. . |
| 4,587,258 | 5/1986 | Gold et al. . |
| 4,772,684 | 9/1988 | Brunck et al. . |
| 4,780,401 | 10/1988 | Heusser et al. . |
| 4,816,463 | 3/1989 | Blankley et al. . |
| 4,845,079 | 7/1989 | Luly et al. . |
| 4,885,292 | 12/1989 | Ryono et al. . |
| 4,894,437 | 1/1990 | TenBrick . |
| 4,980,283 | 12/1990 | Huang et al. . |
| 5,034,512 | 7/1991 | Hudspeth et al. . |
| 5,036,054 | 7/1991 | Kaltenbronn et al. . |
| 5,055,466 | 10/1991 | Weller, III et al. . |
| 5,063,053 | 11/1991 | Himmelsbach et al. . |
| 5,063,207 | 11/1991 | Doherty et al. . |

(List continued on next page.)

FOREIGN PATENT DOCUMENTS

| | | |
|---|---|---|
| 0253310 | 1/1988 | European Pat. Off. . |
| 0320205 | 6/1989 | European Pat. Off. . |
| 0366033 | 10/1989 | European Pat. Off. . |
| 0434249 | 6/1991 | European Pat. Off. . |
| 0499414 | 8/1992 | European Pat. Off. . |
| WOA8606379 | 11/1986 | WIPO . |

OTHER PUBLICATIONS

Pfeffer, M.A. et al., "A Symposium: Ventricular Remodeling and Unloading following Myocardial Infarction"; Nov. 18, 1991; Am. J. of Cardiology.

Sharpe, N. et all, "Treatment of Patients with Symptomless Left Ventricular Dysfunction after Myocardial Infarction"; Feb. 6, 1988; pp. 255–259; The Lancet.

Swedberg K, for the Consensus 11 Trial Study Group. Lack of beneficial effects on mortality by early intervention with enalapril in acute myocardial infarction. Goteborg, Sweden. Circulation, Supplement 11. 84(4):1457–8, 1991.

Sweet C. Issues surrounding a local cardiac renin system and the beneficial actions of angiotensin–converting enzyme inhibitors in ischemic myocardium. Am J Cardiol 65:111–131, 1990.

Ertl G, Guadron P, Kochsiek K. Influence of angiotensin- –converting enzyme inhibition on cardiac function in myocardial infarction. Am J Cardiol. 65:70G–73G, 1990.

Ray S, McAlpine H, Morton J, Leckie B, Dargie H. Importance of RAA system and the treatment of patients with ACE inhibition after myocardial infarction. Angiology. 42(4):268–272, 1991.

Michel J, Lattion A, Salzmann J, de Lourdes Cerol M, Philippe M, Camilleri J, Corvol P. Hormonal and cardiac effects of converting enzyme inhibition in rat myocardial infarction. Circ Res. 62(4):641–650, 1988.

Litwin S, Litwin C, Raya T, Warner A, Goldman S. Contractility and stiffness of noninfarcted myocardium after coronary ligation in rats: effects of chronic angiotensin converting enzyme inhibition. Circulation. 83(3):1028–37, 1991.

Sharpe N, Smith H, Murphy J, Greaves S, Hart H, Gamble G. Early prevention of left ventricular dysfunction after myocardial infarction with angiotensin–converting–enzyme inhibition. Lancet. 337:872–76, 1991.

Pinto Y, Wijngaarden J, van Gilst W, de Graeff P, Wesseling H. The effects of short–and long–term treatment with an ACE–inhibitor in rats with myocardial infarction. Basic Res Cardiol. 86(Suppl 1):165–72, 1991.

van Krimpen C, Shoemaker R, Cleutjens J, Smits J, Struyker–Boudier H, Boman F, Daemen M. Angiotensin I converting enzyme inhibitors and cardiac remodeling. Basic Res Cardiol. 86(Suppl 1):149–55, 1991.

Clozel J. Effects of chronic heart failure on the responsiveness to angiotensin I and to angiotensin converting enzyme inhibition with cilazapril in rats. Br J Clin Pharmac. 27:167S–174S, 1989.

(List continued on next page.)

Primary Examiner—Theodore J. Criares
Attorney, Agent, or Firm—Wolf, Greenfield & Sacks, P.C.

[57] ABSTRACT

The invention involves a method for treating a human survivor of a heart attack and provides further improvement in survival following the heart attack by the early initiation and long-term administration of a renin-angiotensin system inhibitor, preferably an angiotensin converting enzyme inhibitor. The inhibitor may be used on its own, or in conjunction with other therapeutic compounds such as data blockers and thrombolytic agents. The preferred inhibitor is captopril.

11 Claims, 8 Drawing Sheets

U.S. PATENT DOCUMENTS

| | | |
|---|---|---|
| 5,063,208 | 11/1991 | Rosenberg et al. . |
| 5,064,825 | 11/1991 | Chakravarty et al. . |
| 5,064,965 | 11/1991 | Ocain et al. . |
| 5,066,643 | 11/1991 | Abeles et al. . |
| 5,071,837 | 12/1991 | Doherty et al. . |
| 5,073,566 | 12/1991 | Lifer et al. . |
| 5,075,451 | 12/1991 | Ocain et al. . |
| 5,081,127 | 1/1992 | Carini et al. . |
| 5,085,992 | 2/1992 | Chen et al. . |
| 5,087,634 | 2/1992 | Reitz et al. . |
| 5,095,006 | 3/1992 | Bender et al. . |
| 5,095,119 | 3/1992 | Ocain et al. . |
| 5,098,471 | 3/1992 | Hanson et al. . |
| 5,098,924 | 3/1992 | Poss . |
| 5,104,869 | 4/1992 | Albright et al. . |
| 5,106,835 | 4/1992 | Albright et al. . |
| 5,114,937 | 5/1992 | Hamby et al. . |
| 5,116,835 | 5/1992 | Rüger et al. . |
| 5,264,447 | 11/1993 | Ohtawa ................................... 514/381 |
| 5,266,583 | 11/1993 | Ohtawa ................................... 514/381 |

OTHER PUBLICATIONS

Dzau V, Creager M. Progress in Angiotensin–converting enzyme inhibition in heart failure: rationale, mechanisms, and clinical responses. Cardiology Clinics. 7(1);1 19–130, 1989.

Howes L, Hodsman G, Rowe P, Johnston C. Comparative effects of angiotensin converting enzyme inhibition (perindopril) or diuretic therapy on cardiac hypertrophy and sympathetic activity following myocardial infarction in rats. Cardiovasc Drugs Ther. 5:147–152, 1991.

Tio R, de Langen C, de Graeff P, van Gilst W, Bel K, Wolters K, Mook P, Wijngaarden J, Wesseling H. The effects of oral pretreatment with zofenopril, an angiotensin– converting enzyme inhibitor, on early reperfusion and subsequent electrophysiologic stability in the pig. Cardiovasc Drugs Ther. 4:695–704, 1990.

Ribout C, Rochette L. Converting enzyme inhibitors (captopril, enalapril, perindopril) prevent early–post infarction ventricular fibrillation in the anaesthetized rat. Cardiovasc Drugs Ther. 1:51–55, 1987.

Michel J. Relationship between decrease in afterload and beneficial effects of ACE inhibitors in experimental cardiac hypertrophy and congestive heart failure. European Heart Journal. 1 1 (Suppl D):1 7–26, 1990.

Pfeffer M. Angiotensin converting enzyme inhibition therapy following myocardial infarction: rationale for clinical trials. Herz. 16:278–282, 1991.

Tobe T, de Langen C, Weersink E, Wijngaarden J, Bel K, de Graeff P, van Gilst W, Wesseling H. The Angiotensin converting enzyme inhibitor peridopril improves survival after experimental myocardial infarction in pigs. Journal of Cardiovascular Pharmacology. 19:732–740, 1992.

Lindpaintner K, Niedermaier N, Drexier H, Ganten D. Left ventricular remodeling after myocardial infarction: does the cardiac renin–angiotensin system play a role? journal of Cardiovascular Pharmacology. 20(Suppl 1):S41–S47, 1992.

Nelissen–Vrancken H, Struijker–Boudier H, Smits J. Renal hemodynamic effects of nonhypotensive doses of angiotensin–converting enzyme inhibitors in hypertension and heart failure rats. Journal of Cardiovascular Pharmacology. 19:163–168, 1992.

Sharpe N. Angiotensin–converting enzyme inhibitors in heart failure: a role after myocardial infarction. Journal of Cardiovascular Pharmacology. 18(Suppl 2):S99–S104/ 1991.

Hall A, Winter C, Bogle S, Mackintosh A, Murray G, Ball S. The acute infarction ramipril efficacy (AIRE) study: rationale, design, organization, and outcome definitions. journal of Cardiovascular Pharmacology. 18(Suppi 2):S1 05–S1 09, 1991.

McMurray J, MacLenachan J, Dargie H. Unique cardioprotective potential of angiotensin converting enzyme inhibitors: a hypothesis still to be tested on humans. Journal of Hypertension. 9:393–397, 1991.

Timmermans P, Wong P, Chits A, Herblin W. Nonpeptide angiotensin 11 receptor antagonists. TIPS. 12:55–62, 1991.

Sharpe N. Early preventive treatment of left ventricular dysfunction following myocardial infarction: optimal timing and patient selection. Am J Cardiol. 68:64D–69D, 1991.

Moye L, Pfeffer M, Braunwaid E for the Save Investigators. Rationale, design and baseline characteristcs of the survival and ventricular enlargement trial. Am J Cardiol. 68:70D–79D, 1991.

ISIS–4 Collaborative Group. Fourth international study of infarct survival: protocol for a large simple study of the effects of oral mononitrate, or oral captopril, and of intravenous magnesium. Am J Cardiol. 68:87D–1 OOD, 1991.

Ambrosioni E, Borghi C, Magnani B for the Smile Pilot Study Working Party. Early treatment of acute myocardial infarction with angiotensin–converting enzyme inhibition: safety considerations. Am J Cardiol. 68:1 01 D–1 1 OD, 1991.

van Gilst W, Kingma J. for the Cats Investigators Group. Early intervention with angiotensin–converting enzyme inhibitors during thrombolytic therapy in actue myocardial infarction: rationale and design of captopril and thrombolysis study. Am J Cardiol. 68:1 1 1 D–1 15D, 1991.

Pfeffer M, Braunwaid E. Ventricular enlargement following infarction is a modifialbe process. Am J Cardiol. 68:127D–1 31 D, 1991.

Fletcher PJ, Pfeffer JM Pfeffer MA, Braunwald E. Left Ventricular diastolic pressure–volume relations in rats with healed myocardial infarction: effects on systolic function. Circ Res. 1981; 49:618–626.

Pfeffer JM, Pfeffer MA, Mirsky I, Braunwald E. Regression of left ventricular hypertrophy and prevention of ventricular dysfunction by captopril in the spontaneously hypertensive rat. Proc Nat'l Acad Sci. 1982; 79:3310–3314.

Ichikawa I, Pfeffer JM, Pfeffer MA, Hostetter TH, Brenner BM. Role of angiotensin II in the altered renal function of congestive heart failure. Circ Res. 1984; 55:669–675.

Pfeffer MA, Pfeffer JM, Steinberg C, Finn P. Survival following an experimental myocardial infarction: beneficial effects of chronic captopril therapy. Circulation. 1985; 72:406–412.

Pfeffer JM, Pfeffer MA, Braunwald E. Influence of chronic captopril therapy on the infarcted left ventricle of the rat. Circ Res. 1985; 57:84–95.

Pfeffer MA, Lamas GA, Vaughn DE, Parisi AF, Braunwald E. Effect of captopril on progressive ventricular dialation after anterior myocardial infarction. N. Engl J. Med. 1988; 319:80–86.

Lamas GA, Vaughn DE, Parisi, AF, Pfeffer MA. Effects of left ventricular shape and captopril therapy on exercise capacity following anterior wall acute myocardial infarction. Am J. Cardiol. 1989; 63:1167–1173.

Pfeffer MA, Braunwald E. Ventricular remodeling after myocardial infarction: Experimentalobservations and clinical implications. Circulation. 1990; 81:1161–1172.

Pfeffer JM, Pfeffer MA, Fletcher PJ, Braunwald E. Progressive ventricular remodeling in the rat with myocardial infarction. Am J Physiol. 1991; 260(Heart Circ. Physiol 29):H1406–H1414.

Lamas GL, Pfeffer MA. Left ventricular remodeling following acute myocardial infarction: clinical course and beneficial effects of angiotensis–converting enzyme inhibition. Am Heart J. 1991; 121:1194–1202.

Pfeffer MA, Braunwald E, Myoe LA, Basta L. Brown Jr. Ej, Cuddy TE, Davis BR, Geltman EM, Goldman S, Falker GC, Klein M, Lamas GA, Packer M, Rouleau J, Rouleau JL, Rutherford J, Wertheimer JH, Hawkins CM, on behalf of the Save Investigators. The effect of captopril on mortality and morbidity in patients with left ventricular dysfunction after myocardial infarction. Results of the Survival and Ventricular Enlargement Trial. N Engl. J. Med. 1991; 327:669–677.

Pfeffer, J.M., et al., Prevention of the development of heart failure and the regression of cardiac hypertrophy by captopril in spontaneously hypertensive rats. Europ Heart J. 1983; 4(Suppl A):143–148.

Pfeffer, J.M., et al. Prevention of cardiac hypertrophy and dysfunction by an angiotensin conversion inhibitor in the spontaneously hypertensive rat. In: Doyle A.E., Bearn, A.G., eds. Hypertension and the Angiotensin System: Therapeutic Approaches. New York: Raven Press, 1984:215–232.

Pfeffer, J.M., et al. Hemodynamic benefits and prolonged survival with long–term captopril therapy in rats with myocardial infarction and heart failure. Circulation. 1987; 75(Suppl 1):1–149–1–155.

Pfeffer, M.A., Pfeffer, J.M. Ventricular enlargement and reduced survival after myocardial infarction. Circulation. 1987; 75(Suppl IV):IV–93–IV–97.

Pfeffer, J.M., Pfeffer, M.A. Angiotensin converting enzyme inhibition and ventricular remodeling in heart failure. Am. J. Med. 1988; 84(Suppl 3a):37–44.

Pfeffer, M.A., et al. Effect of captorpil on ventricular dilation after anterior myocardial infarction. N. Engl. J. Med. 1988; 319–1736.

Pfeffer, M.A. Ventricular enlargement after myocardial infarction: status of ACE inhibition. In: Sonnenblick, E.H. Laragh, J.H., Lesch M. eds. New Frontiers in Cardiovascular Therapy: Focus on Angiotensin Converting Enzyme Inhibition. Princeton, New Jersey: Excerpta Medica, An Elsvier Company, 1989:286–290.

Pfeffer, M.A. Angiotensin–Converting Enzyme Inhibtion. In: Topol, E.M., ed. Textbook of Interventional Cardiology. Orlando: WB Saunders Co., 1990:66–75.

Pfeffer, M.A. ACE inhibitors and ventricular remodeling following myocardial infarction. Choices in Cardiology. 1991; 5(SI):3–5.

Pfeffer, M.A. Angiotensin converting enzyme inhibition therapy following myocardial infarction: Rationale for clinical trials. Herz. 1991; 16:278–282.

Gaudron, P., et al. Early remodeling of the left ventricle in patients with myocardial infarction. Europ Heart J. 1990; 11 (Suppl B):139–46.

Packer, M., et al. Effect of oral milrinone on mortality in sever chronic heart failure. N. Engl. J. Med. 1991; 325:1468–1475.

Jeremy, R.W., et al. Patterns of left ventricular dilation during the six months after myocardial infarction. J. Am. Coll. Cardiol. 1989; 13:304–10.

Sharpe, N., et al. Treatment of patients with symptomsless left ventricular dysfunction after myocardial infarction. Lancet 1988; 1:255–9.

Nabel, E.G. et al. A randomized placebo–controlled trial of combined early intravenous captopril and recombinant tissue–type plasminogen activator therapy in acute myocardial infarction. J. Am. Coll. Cardiol. 1991; 17:467–73.

Consensus Trial Study Group. Effects of enalapril on mortality in severe congestive heart failure. Results of the Cooperative North Scandinavian Enalapril Survival Study (Consensus). N. Engl. J. Med. 1987; 316:1429–35.

Cohn, J.N., et al. Effect of vasodilator therapy on mortality in chronic congestive heart failure. Results of a Veterans Administration Cooperative Study. N. Engl. J. Med. 1986; 314:1547–52.

The SOLVD Investigators. Effect of enalapril on survival in patients with reduced left ventricular ejection fractions and congestive heart failure. N. Engl. J. Med. 1991; 325:293–302.

Packer, M., et al. Role of neurohormonal mechanisms in determining survival in patients with severe chronic heart failure. Circulation 1987; 75 (Suppl IV):IV–80–IV–92.

Sussex, B.A., et al. Independent and interactive prognostic information of neurohormones and echocardiogram in high risk post–MI patients. J. Am. Coll. Cardiol. 1992; 19:205A (Abstract).

Moye, L.A., et al. Analysis of a clinical trial involving a combined mortality and adherence dependent interval censored endpoint. Statistics in Medicine 11:1705–1717 (1992).

The Multicenter European Research Trial With Cilazapril After Angioplasty to Prevent Transluminal Coronary Obstruction and Restenosis (Mercator) Study Group. Does The New Angiotensin Converting Enzyme Inhibitor Cilazapril Prevent Restenosis After Percutaneous Transluminal Coronary Angioplasty? Circulation 1992; 86:1, 100–110.

ACC/AHA Task Force Report, Guidelines For The Early Management Of Patients With Acute Myocardial Infarction, JACC vol. 16, No. 2 Aug. 1990: 249–292.

Myocardial Infarction and its Attenuation by Angiotensin–converting Enzyme Inhibition, Nov. 18, 1991, pp. 17D–25D, American Journal of Cardiology, V. 68., No. 14.

Ambrosioni, E. et al., "Early Treatment of Acute Myocardial Infarction with Angiotensin–Converting Enzyme Inhibition, Safety Considerations", 1991, pp. 101D–110D, Am. J. of Cardiology, V. 68.

METHODS FOR REDUCING RISK OF REPEAT MYOCARDIAL INFARCTION AND INCREASING SURVIVAL IN HEART ATTACK VICTIMS

RELATED APPLICATION

This application is a continuation-in-part of U.S. Ser. No. 07/866,827 filed on Apr. 10, 1992, the disclosure of which is incorporated herein by reference.

Survivors of acute myocardial infarction are at greatly increased risk for subsequent fatal and non-fatal cardiovascular events (1). This heightened risk is not a uniform one, but rather is influenced by many factors such as age, co-morbid diseases, extent of coronary artery disease, electrical stability, and, most importantly, the severity of left ventricular dysfunction. Irrespective of how the latter is measured (ventricular volumes, ejection fraction, contraction score), the severity of dysfunction correlates highly with mortality and thus is useful in stratifying survivors of acute myocardial infarction into categories of varying risk (2,3,4,5). Of these indices of left ventricular impairment, the most powerful predictor of survival is ventricular volume (4,5).

In a rat model of myocardial infarction produced by ligation of the left coronary artery, progressive left ventricular dilation has been shown to occur as a function of the size and age of the infarct (6,7). During the acute post-infarction phase, prior to scar formation, an increase in ventricular diastolic volume occurs as a consequence of infarct expansion and a rise in filling pressure (8,9). Following formation of a discrete scar, left ventricular dilation may continue as the result of a remodeling of the residual viable myocardium, initially acting to restore stroke volume (9,10). If the infarct is of sufficient size, the increase in diastolic volume may progress, leading to further deterioration in ventricular performance and perpetuation of the dilatation (11). In a rat model of myocardial infarction, the chronic administration of the angiotensin converting enzyme inhibitor, captopril, has been shown to attenuate this gradual dilatation of the left ventricle both by remodeling its structure and reducing its distending pressure, leading to an improvement in cardiac function (12) and, in long-term studies, a prolongation of survival (12,13).

Although this animal data is encouraging, it is by no means predictive of what will happen in humans. In fact, the NIH has been critical of pre-clinical data based upon rat models (personal communication), and a recent clinical trial based upon rat data of improved survival with therapy using an angiotensin converting enzyme inhibitor (milirone) resulted in an opposite conclusion (excess death) in humans (14). In still another study, an angiotensin converting enzyme inhibitor (cilazapril) was ineffective in preventing restenosis following coronary angioplasty in humans, despite the efficacy of cilazapril in preventing restenosis in a rat model (15). We believe further that it is impossible to extrapolate from rat studies to humans in connection with coronary artery disease because rats do not actually have coronary artery disease. They also do not have the associated medical problems following human myocardial infarction that require concomitant therapies, further confounding any attempted exptrapolation.

Recently, several clinical studies have confirmed the progressive nature of left ventricular enlargement and dysfunction in patients during the late phase following a myocardial infarction (10,16). So too has chronic therapy with angiotensin converting enzyme inhibition been shown to attenuate ventricular enlargement and prevent a further deterioration of performance in this patient population (17, 18). Although the endpoints in these studies, e.g., ventricular size and function, were well-defined, the sample sizes were too small to address the critical clinical issue, i.e., the influence of angiotensin converting enzyme inhibitor therapy on long-term survival and clinical outcome.

One recent study, initiated after ours, set out to test whether treatment for six months with an angiotensin converting enzyme inhibitor (enalapril) might have a beneficial effect on mortality in patients who have had myocardial infarction. That study concluded that there was no beneficial effect on mortality. In fact, the study was terminated "because of a recommendation of the safety committee" (19).

It is an object of the invention to provide a method for increasing the chances of survival in humans who have had a heart attack.

Another object of the invention is to provide a method for lessening deterioration in cardiac performance and improving clinical outcome in human survivors of a heart attack.

SUMMARY OF THE INVENTION

The invention involves treating a human survivor of a heart attack by administering a therapeutically effective amount of a renin-angiotensin system inhibitor. This treatment is intended for patients who are otherwise free of indications for a renin-angiotensin system inhibitor. The invention reduces the chances of adverse health consequences that occur following a heart attack.

Preferably, the renin-angiotensin system inhibitor is a renin inhibitor, an angiotensin converting enzyme inhibitor or an angiotensin II antagonist. At least in the case of angiotensin converting enzyme inhibitor, it is preferred that the administration be early and long-term. It is desirable, however, to begin such treatment only after three days have elapsed from the date of the heart attack, and it further is desirable to gradually increase the dose. Most preferably, the angiotensin converting enzyme inhibitor is captopril.

The renin-angiotensin system inhibitor may be used alone or in conjunction with other compounds that are known to reduce adverse health consequences that occur following a heart attack. For example, the beneficial results of treatment with captopril are present when captopril is administered in conjunction with either beta-adrenergic blocking agents Aspirin or thrombolytic agents.

These and other aspects of the invention will be described in greater detail below.

DETAILED DESCRIPTION OF THE PREFERRED EMBODIMENTS

Figure 1:
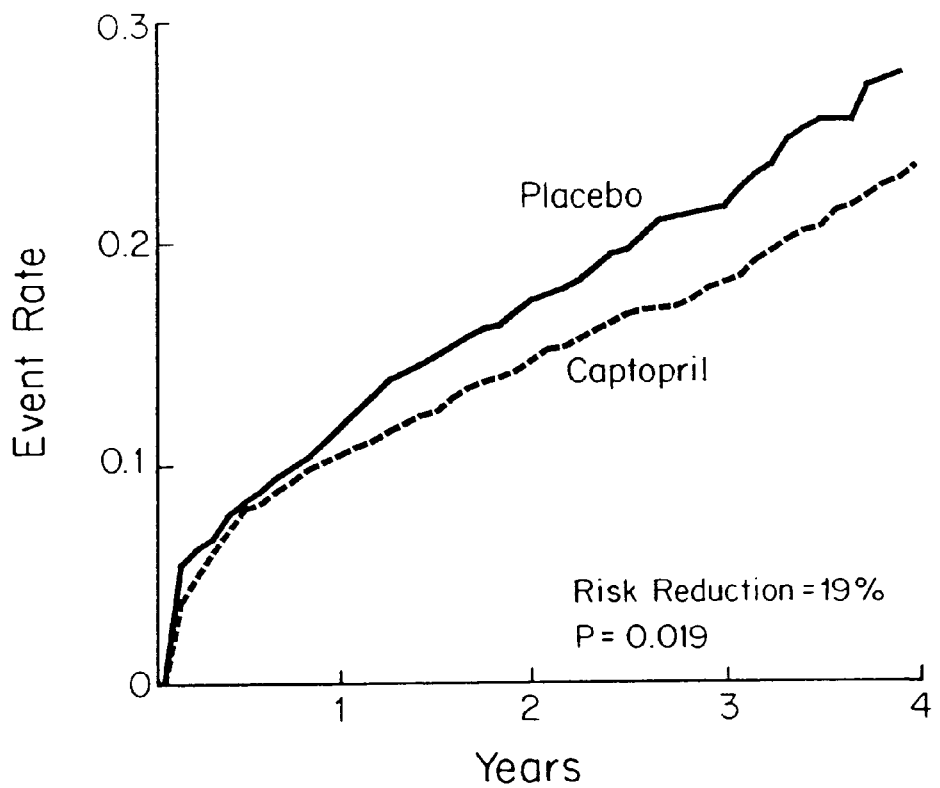
FIG. 1 is a graph depicting all cause mortality for placebo treated survivors compared to captopril treated survivors.

The present invention provides a treatment for heart attack survivors. It involves therapy with a renin-angiotensin system inhibitor, preferably an angiotensin converting enzyme inhibitor, in survivors with depressed left ventricular ejection fraction but without overt heart failure, and it can result in reductions in total and cardiovascular mortality, in the frequency of development of severe congestive heart failure and of recurrent myocardial infarction, and in the proportion of patients who either died or survived with a marked deterioration in left ventricular ejection fraction.

The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

An overview of the pathway for synthesis of the angiotensins in vivo is as follows. The process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1–8] octapeptide). The latter is an active pressor substance which has been implicated as the causative agent in several forms of hypertension in various mammalian species, e.g., humans.

Renin-angiotensin system inhibitors as defined herein are compounds that act to interfere with the production of angiotensin II from angiotensinogen or to interfere with the activity of angiotensin II. Such inhibitors are well known to those of ordinary skill in the art and include compounds that act to inhibit the enzymes involved in the production of angiotensin II, including renin and ACE. They also include compounds that act on the substrates of these enzymes and compounds that interfere with the activity of angiotensin II, once produced. Examples of classes of such compounds include antibodies (e.g. to renin or to ACE), amino acids and analogs thereof (including those conjugated to larger molecules), peptides (including peptide analogs of angiotensinogen and angiotensin I), pro-renin related analogs, phospholipids and more. Among the most potent and useful renin-angiotensin system inhibitors are renin inhibitors, ACE inhibitors and angiotensin II antagonists.

Renin inhibitors are well known and include amino acids and derivatives thereof, peptides and derivatives thereof and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5114,937); di-and tri-peptide derivatives (U.S. Pat. No. 5,106,835); amino acids and derivatives thereof (U.S. Pat. Nos. 5,104, 869 and 5,095,119); diol sulfonamides and sulfinyls (U.S. Pat. No. 5,098,924); modified peptides (U.S. Pat. No. 5,095, 006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. No. 5,063,208 and U.S. Pat. No. 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. No. 5,071,837, U.S. Pat. No. 5,064,965, U.S. Pat. No. 5,063,207, U.S. Pat. No. 5,036,054, U.S. Pat. No. 5,036,053, U.S. Pat. No. 5,034,512, and U.S. Pat. No. 4,894,437).

ACE inhibitors intervene in the angiotensin (renin) angiotensin I angiotensin II sequence by inhibiting angiotensin converting enzyme and reducing or eliminating the formation of the pressor substance angiotensin II. ACE inhibitors are useful as antihypertensive agents and for treating congestive heart failure.

ACE inhibitors are well known and include amino acids and derivatives thereof, peptides including di- and tri-peptides and antibodies to ACE. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (Id.), quinapril (U.S. Pat. No. 4,344, 949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazepril (U.S. Pat. No. 4,410,520), phosphinylalkanoyl prolines such as fosinopril (U.S. Pat. No. 4,337,201) and trandolopril.

Angiotensin II inhibitors are compounds that interfere with the activity of angiotensin II. Angiotensin II inhibitors include angiotensin II antagonists and antibodies to angiotensin II. Preferred are the $AT_1$ specific antagonists. Angiotensin II antagonists are well known and include peptide compounds and nonpeptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g. saralasin, [$San^1$, $Val^5$, $Ala^8$] angiotensin-(1–8) octapeptide and related analogs); N-substituted imidazole-2-one (U.S. Pat. No. 5,087,634); imidazole acetate derivatives including 2-n-butyl-4-chloro-1-(2-chlorobenzyl) immidazole-5-acetic acid (see Wong et al., *J. Pharmacol. Exp. Ther.* 247 (1), 1–7 (1988)); 4, 5, 6, 7-tetrahydro-1H-imidazo [4,5-c] pyridine-6-carboxylic acid and analogs derivatives (U.S. Pat. No. 4,816,463); N 2-tetrazole beta-glucuronide analogs (U.S. Pat. No. 5,085, 992); substituted pyrroles, pyrazoles and triazoles (U.S. Pat. No. 5,081,127); phenyl and heterocyclic derivatives such as 1,3-imidazoles (U.S. Pat. No. 5,073,566); imidazo-fused 7-member ring heterocycles (U.S. Pat. No. 5,064,825); peptides (e.g. U.S. Pat. No. 4,772,684); antibodies to angiotensin II (e.g. U.S. Pat. No. 4,302,386); and aralkyl imidazole compounds such as biphenyl-methyl substituted imidazoles (e.g. EP no. 253,310, Jan. 20, 1988). Other angiotensin II inhibitors currently being tested include ES-8891 (N-morpholinoacetyl-(-1-naphtyl)-L-alanyl-(4-thiazolyl)L-alanyl(35, 45)-4-amino-3-hydroxy-5-cyclohexapentanoyl-n-hexylamide, Sankyo Company Ltd., Tokyo, Japan), SK&F 108566 (E-α-2-[2-butyl-1-[(carboxyphenul) methyl]1H-imidazol-5-yl]methylanel-2-thiophenepropanoic acid, SmithKline Beecham Pharmaceuticals, Pa.), Losartan (DUP 753/MK 954, DuPont Merck Pharmaceutical Co.), Remikirin (RO 42-5892, F. Hoffmann LaRoche AG), Adenosine $A_2$ agonists (Marion Merrell Dow) and certain nonpeptide heterocycles (G.D. Searle & Company).

(The disclosures of the foregoing patents relating to renin inhibitors, ACE inhibitors and angiotensin II inhibitors are incorporated herein by reference.)

The foregoing compounds never before have been given early and for extended periods of time to heart attack survivors who are otherwise free of indications for renin-angiotensin system inhibitors. By "free of indications for renin-angiotensin system inhibitors", it is meant that the survivor does not have symptoms or a clinical history that call for treatment with an a renin-angiotensin system inhibitor (other than the indication which exists as a result of this invention). In other words, treatment is given to survivors who do not exhibit, among other things, symptomatic congestive heart failure, or systemic hypertension, or specifically in the case of a renin inhibitor, hyperaldosterism, glaucoma, diabetic neprophathy and certain diseases caused by retrovirus including HTLV-I, II and III. By "long-term" or "extended period" it is meant greater than six months. Preferably, the renin-angiotensin system inhibitor is administered continuously and substantially without interruption for at least two years.

In the preferred embodiment, an ACE inhibitor is employed, and the ACE inhibitor is not administered to the survivor immediately following the heart attack. Instead, the start of medication is delayed for several days, preferably three. In addition, it is preferred that the survivor first receive a relatively low dose of the ACE inhibitor, gradually increasing that dose to the maximum tolerable dose. By "maximum" dose, it is meant the highest dose that is free of medically unacceptable side effects, i.e., the highest safe dose according to sound medical judgment. By "tolerable" dose, it is meant the highest dose that a patient is willing to take. It thus will be understood by those of ordinary skill in the art that although the maximum dose may be preferred, any particular survivor may insist on a lower dose for medical reasons, for psychological reasons or for virtually any other reason.

In the most preferred embodiment, the ACE inhibitor is a tablet containing captopril (U.S. Pat. No. 4,105,776, sold by Bristol-Myers Squibb). The captopril is administered orally in tablet form, beginning three days after the heart attack (and preferably not later than sixteen days after the heart attack). It is administered first at a dose of less than 20 mg per day, and gradually increased to the maximum dose of 150 mg per day. Preferably the captopril is administered three times per day to achieve these doses.

Somewhat surprisingly, the renin-angiotensin system inhibitor still achieves a beneficial effect when co-administered with non-system inhibitor compounds that reduce the risk of adverse health consequences occurring after a heart attack. For example, aspirin, beta-adrenergic blocking agents, anticoagulants and thrombolytic agents are known to produce beneficial effects when administered to heart attack survivors. When the ACE inhibitors are co-administered with such compounds, the effect is cumulative; that is, the beneficial effects of the invention are present over and above the beneficial effects of the other compounds.

The renin-angiotensin system inhibitor may be administered by any medically-acceptable route, including oral, rectal, topical, nasal, transcutaneous or parenteral (e.g., subcutaneous, intermuscular and intravenous) routes. The preferred route is oral. Formulations of the inhibitor suitable for oral administration include discrete units such as capsules, tablets, lozenges and the like. The preferred formulation is a tablet.

The renin-angiotensin system inhibitors are administered in therapeutically effective amounts. By "therapeutically effective amount", it is meant that amount necessary to achieve a reduction in the risk of adverse health consequences. Adverse health consequences include congestive heart failure, recurrent myocardial infarction and/or death. The effective amount will vary according to the particular ACE inhibitor used and the mode of administration. It also may vary according to individual patient parameters including age, physical condition, size and weight. These factors are well-known to those of ordinary skill in the art and can be suitably addressed with no more than routine experimentation.

Typically, the dose range is from 1–1000 mg/kg body weight per day. Generally, treatment is initiated with dosages that are less than the optimum dose. Thereafter the dose is increased. The total daily dose can be administered is portions during the day, if desired.

As will be demonstrated in the example to follow, the early initiation and continued administration of an ACE inhibitor, captopril, to patients with asymptomatic left ventricular dysfunction following an acute myocardial infarction improved long-term overall survival and reduced the mortality and morbidity due to major cardiovascular events. In particular, overall deaths were reduced; congestive heart failure requiring ACE inhibitor treatment was reduced; and congestive heart failure requiring hospitalization was reduced. Additionally, of the patients who developed congestive heart failure, survival was improved for those who had been receiving the ACE inhibitor prior to developing the symptoms of congestive heart failure.

EXAMPLE

Study Organization

The trial was a randomized, double-blind, placebo-controlled trial of 2231 patients with an acute myocardial infarction and left ventricular dysfunction who were enrolled at 45 clinical centers.

Patient Recruitment

The enrollment phase of the trial began on Jan. 27, 1987 and ended on Jan. 28, 1990. To be considered for recruitment, patients of either gender had to survive the first three days of a myocardial infarction with a radionuclide left ventricular ejection fraction $\leq 40$ percent and be at least 21 but under 80 years of age. A myocardial infarction was considered to have occurred if the patient experienced either (1) acute changes in an electrocardiogram (Q or QS finding plus ST elevation and/or T-Wave inversion plus absence of left bundle branch block or Wolff-Parkinson-White syndrome) obtained shortly after the infarction with the attendant clinical symptoms and elevation in myocardial enzymes or (2) the presence of changes in Q-waves on serial electrocardiograms demonstrated a myocardial infarction had occurred or (3) the patient had an elevation of myocardial enzymes that were twice as high as normal levels and typical symptoms of a myocardial infarction were present.

Exclusions to enrollment included: women of child bearing potential unless contraception was used; patients with malignancy thought to reduce survival or requiring radiation therapy; severe valvular heart disease likely to require a surgical procedure; psychologic disorder making the patient unsuitable for a clinical trial; participation in another investigational drug trial; clinical ischemia with no corrective procedure prior to the scheduled time of randomization; ischemia or symptomatic hypotension following the test dose of captopril; failure to randomize within 16 days of the myocardial infarction; relative contraindication to the use of an angiotensin converting enzyme inhibitor or its requirement for the management of symptomatic congestive heart failure or systemic hypertension; a serum creatinine level >221 µmol/liter (2.5 mg/dl); other conditions thought to limit survival; an unwillingness or inability to participate in a long-term trial; and an unstable course following infarction.

The presence of recurrent ischemic discomfort 72 hours after the onset of the index myocardial infarction, a positive exercise test ($\geq 2$ mm ST segment depression and failure to complete the modified exercise protocol), required that cardiac catheterization and coronary arteriography be performed and a clinical decision made regarding the need for myocardial revascularization. If required, revascularization had to be performed so as to allow patients to be randomized three to 16 days post-infarction. Of the 8938 patients considered eligible by this initial screening process, 2250 (25.2 percent) had no exclusions and consented to participate in the trial. Prior to randomization, all eligible and consenting patients were given a test dose of open-label captopril 6.25 mg orally. If this initial dose was well tolerated and not associated with significant orthostatic or ischemic symptoms, the patient was randomized to receive either captopril or placebo therapy in a double-blind fashion.

The test dose of 6.25 mg (p.o.) of captopril resulted in the exclusion of 3 patients for associated ischemic discomfort and 16 patients for symptomatic hypotension, yielding a study population of 2231. A more detailed presentation of the screening process and the exclusions to enrollment has been published in The American Journal of Cardiology (19), the entire disclosure of which is incorporated herein by reference.

Randomization, Dose Titration, and Follow-up

Randomization to therapy with either placebo or captopril was achieved by computer-generated allocation and was stratified by center. Two additional stratifications, based on age (above and below 70 years) and left ventricular ejection fraction (above and below 20 percent), insured that the subsets of patients (age above 70 years and/or ejection fraction below 20 percent) who were at highest risk for adverse events would be evenly distributed between the two therapy groups. The initial dose of the blinded medication was 12.5 mg. However, investigators were allowed to administer a 6.25 mg dose to those patients who had a marked, yet asymptomatic reduction in blood pressure with the test dose. The target dose of study medication was 25 mg three times daily by the end of the in-hospital phase and was titered to a maximum of 50 mg three times daily following discharge from the hospital. If the investigator perceived any adverse experience to the medication, a reduction in dose was permitted. Outpatient visits were begun two weeks after randomization, then scheduled at intervals of three months during the first year of follow-up and at intervals of four months during the remainder of the trial. All patients were followed for a minimum of two years.

At each follow-up visit, a physical examination was performed and interim clinical events were ascertained. Symptoms of myocardial ischemica were noted as was the development of signs and symptoms of congestive heart failure. Patients were categorized according to the presence of severe congestive heart failure at any time during the follow-up period. Assessed, in addition, were the occurrence of recurrent myocardial infarction as well as possible adverse effects of study medication. During the last ten months of follow-up, all surviving patients were to have a repeat radionuclide ventriculogram. The protocol call for temporary (48 hours) suspension of the study medication prior to repeat determination of the ejection fraction; study medication then was resumed and continued for the remainder of the trial. On average, this repeat ejection fraction was obtained 36 months (range, 15 to 57 months) following randomization.

End Points

Observation was continued to the planned completion date of Jan. 31, 1992, by which time the last patient enrolled had finished a minimum follow-up of severe congestive heart failure or the recurrence of a fatal or non-fatal myocardial infarction; and the combination of cardiovascular mortality and morbidity. Two endpoints of severe heart failure (treatment failure) were prospectively defined: 1) patients who developed and remained in overt heart failure despite the administration of diuretics and digitalis and who therefore required angiotensin converting enzyme inhibition therapy. After determining that the patient could not be managed adequately by conventional therapy (diet, diuretics and/or digitalis), the study medication (placebo or captopril) was discontinued in order to initiate therapy with open-label angiotensin converting enzyme inhibitor (for the already approved use for symptomatic heart failure); and, 2) failure of outpatient treatment and consequent hospitalization for the management of congestive heart failure.

The change in radionuclide ventricular ejection fraction was selected as an objective measure that was anticipated to occur infrequently, but when present was deemed to be of major clinical significance. It was determined that a change of 9 percentage points would signify a decrease that was unlikely to be due to chance alone. In addition, observations of repeat radionuclide ventricular ejection fraction period of two years. Several prospectively defined measures of outcome served as end points in the trial: all cause mortality[1]; cardiovascular mortality; mortality combined with a fall in ejection fraction of at least 9 units in survivors; cardiovascular morbidity, defined as the development determinations confirmed that patients with ejection fraction deteriorations greater than or equal to 9% were experiencing an increased risk of death, making this magnitude of deterioration clinically relevant.

[1] Patients who required cardiac transplantation were included in all cause mortality and classified with those who experienced cardiovascular death.

Statistical Analysis

The statistical method has been described in detail previously (20). A sample size of 2200 patients was estimated. All analyses were as intention to treat and all P values were two-sided. Comparability of base-line characteristics of the two treatment groups was ascertained by chi-square tests for categorical variables and standard normal (z) tests for continuous variables. A proportional hazards regression model with time-dependent covariates was used to assess the relative risk of death for patients who experienced heart failure requiring therapy with open-label angiotensin converting enzyme inhibitor or hospitalization. A chi-square test statistic for comparing the occurrence of endpoints across a treatment group was performed and its results are displayed in the text and tables. The analysis of the combined endpoint of the occurrence of either death or survival and a ≧9 unit reduction in ejection fraction, which considered the time to death or a change of ≧9 units of ejection fraction in survivors, was based on the Gehan statistic (21). Kaplan-Meier estimates were used to assess the differences in the distributions of time from randomization to the clinical event of interest as displayed in the life table figures (1 and 3). The log-rank test statistic was used to analyze the life-table date by therapy assignment for the first four years of follow-up.

Results

The 2231 patients enrolled in the trial were followed for an average of 43±10 months, from the prospectively defined minimum of 24 months to a maximum of 60 months. At the completion of this follow-up period, the vital status of 6 patients (4 placebo and 2 captopril) had not yet been ascertained. There were no differences in the characteristics of the patients assigned to placebo or of captopril at the time just prior to randomization. Blood pressure increased in both treatment groups from base line to three months, albeit to differing extents, so that both systolic and diastolic pressures of the placebo group were significantly higher than those in the captopril group at three months. This difference was maintained during follow-up (one-year visit for placebo, 125±18/77±10 and for captopril, 119±18/74±10 mmHg; P<0.001, for both systolic and diastolic pressures). The heart rate for both groups was, on average, 72 beats per minute.

Mortality

From the onset (Jan. 27, 1987) to the termination (Jan. 31, 1992) of the trial, there were 503 deaths, of which 275 of 1116 (24.6 percent) were in the placebo group and 228 of 1115 (20.4 percent) in the captopril group; the reduction in risk for all cause mortality was 19 percent (95 percent confidence interval, 3 to 32 percent; P=0.019) (FIG. 1, Table 1).

A repeat ejection fraction was obtained in 1644 of the 1728 surviving patients [96 percent (806/841) of those on placebo and 95 percent (838/887) of those on captopril] and a deterioration of 9 or more units was noted in 15 percent (125/806) of the patients in the placebo group and in 13 percent (110/838) of the patients in the captopril group (P=0.168). When this measure of progressive left ventricular dysfunction was combined with all cause mortality, this prospectively defined endpoint was realized in 36 percent (400/1116) of patients on placebo and in 30 percent (338/1115) of patients on captopril; the reduction in risk was 15 percent (95 percent confidence interval, 5 to 25 percent; P=0.006) (Table 1).

TABLE 1

Total Mortality and Survival with Deterioration in Left Ventricular Ejection Fraction According to Treatment Group.

| Event | Placebo (N = 1116) number | Captopril (N = 1115) (percent) | Risk Reduction (95% CI) percent | P Value |
|---|---|---|---|---|
| All Cause Mortality | 275 (24.6) | 228 (20.4) | 19 (3 to 32) | 0.019 |
| Alive and Observed Reduction LVEF ≧ 9 Units | 125 (16) | 110 (13) | 11 (−13 to 30) | 0.303 |
| Death of Reduction | 400 (36) | 338 (30) | 15 (5 to 25) | 0.006 |

Death or survival with an observed reduction in left ventricular ejection fraction (LVEF) of ≧ 9 units was also compared with a modified Gehan (18) statistic which considers duration between ejection fraction determinations as well as duration of survival. This analysis also demonstrated a significant improvement in this endpoint for patients randomized to captopril (p = 0.019).

Of the total mortality, 84 percent (422/503) of the deaths were secondary to cardiovascular events, 234 in the placebo group and 188 in the captopril group; the reduction in risk was 21 percent (95 percent confidence interval, 5 to 35 percent; P=0.014) (Table 2). Within this category of cardiovascular death there was a marked reduction in mortality due to cardiac pump failure in the captopril group when compared with the placebo group (58 deaths in the placebo group versus 38 in the captopril group; these 96 deaths included the twelve patients who underwent cardiac transplantation, 7 in the placebo group and 5 in the captopril group); the reduction in risk from cardiac pump failure was 36 percent (95 percent confidence interval, 4 to 58 percent; P=0.032). Non-cardiovascular causes accounted for 16 percent of total mortality and were distributed evenly between the two treatment groups (Table 2). Specifically, there were no differences between the placebo and captopril groups in deaths due to neoplasm, including gastrointestinal neoplasm.

TABLE 2

Causes of Death in the Study Patients.*

| CAUSE OF DEATH | PLACEBO no. of deaths | CAPTOPRIL | RISK REDUCTION (95% CI) percent | P VALUE |
|---|---|---|---|---|
| Cardiovascular | 234 | 188 | 21 (5–35) | 0.014 |
| Atherosclerotic heart disease | 222 | 174 | 23 (6–37) | 0.009 |
| Progressive heart failure† | 58 | 38 | 36 (4–58) | 0.032 |
| Sudden, with preceding symptoms | 50 | 43 | — | NS |
| Sudden, unexpected | 75 | 62 | — | NS |
| Acute myocardial infarction | 25 | 24 | — | NS |
| Cardiac procedure | 9 | 5 | — | NS |

TABLE 2-continued

Causes of Death in the Study Patients.*

| CAUSE OF DEATH | PLACEBO | CAPTOPRIL | RISK REDUCTION (95% CI) | P VALUE |
|---|---|---|---|---|
| | no. of deaths | | percent | |
| Other cardiac | 5 | 2 | — | NS |
| Vascular | 12 | 14 | — | NS |
| Noncardiovascular | 4 | 40 | — | NS |
| Cancer | 20 | 14 | — | NS |
| Infection or gastrointestinal bleeding | 18 | 16 | — | NS |
| Traumatic or unknown | 3 | 10 | — | NS |
| All | 275 | 228 | 19 (3–32) | 0.019 |

*CI denotes confidence interval, and NS not significant.
†Death was attributed to progressive heart failure if it occurred during a hospitalization for management of heart failure or if it was preceded by a recent deterioration in clinical status attributed to heart failure.

Cardiovascular Morbidity

Figure 2:
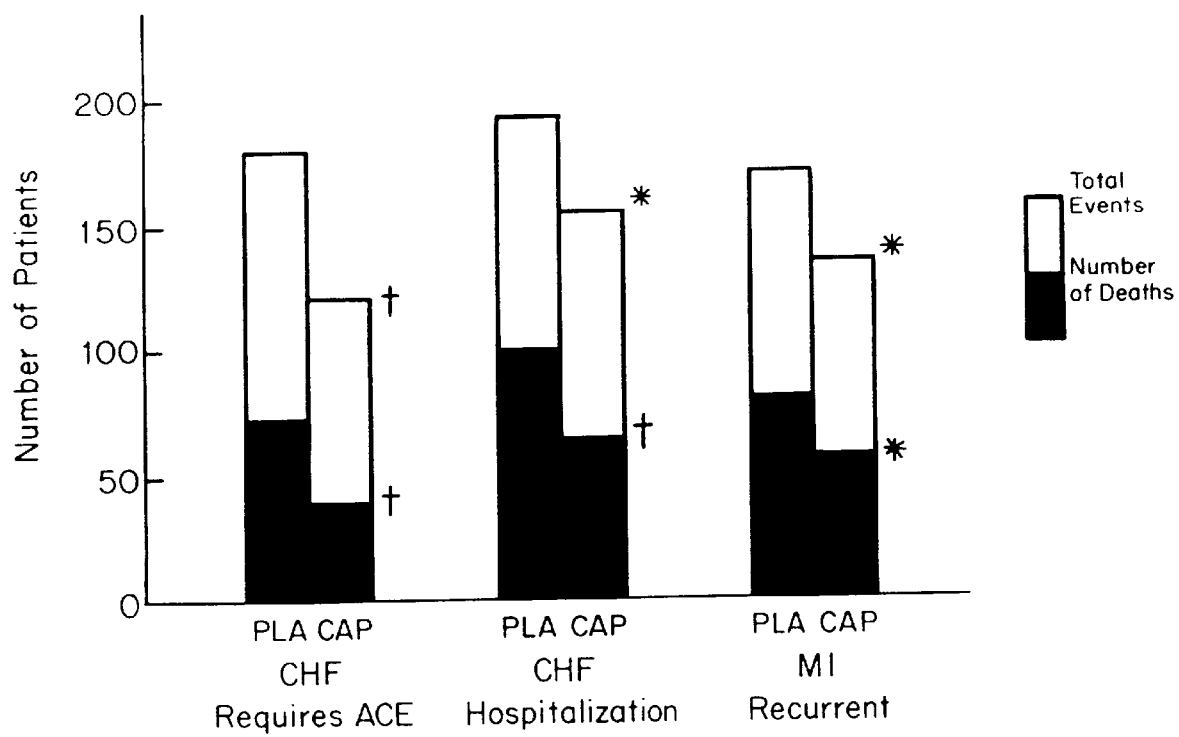
FIG. 2 is a bar graph depicting adverse health consequences for placebo treated survivors compared to captopril treated survivors.

FIG. 2 is a bar graph depicting cardiovascular morbidity and mortality in the captopril and placebo groups. The total bar represents the number of patients experiencing the event in each group and the symbol designates a significant reduction in the event for captopril-treated patients. The lower solid portion of each bar represents the number of patients who manifested the specific cardiovascular event and subsequently died; the symbol next to the solid bar designates a significant reduction in the mortality of the captopril-treated patients experiencing the event (*P<0.05;+ P<0.005).

The incidence of failure of treatment of congestive heart failure with digitalis and diuretics requiring open-label therapy with angiotensin converting enzyme inhibitor increased progressively during the average 43 months of follow-up: 13 percent (297/2231) of the enrolled population manifested this degree of heart failure (FIG. 2). Irrespective of therapy assignment, this need for the use of open-label angiotensin converting enzyme inhibitor was associated with an increased risk of death: 37 percent (110/297) of those patients who exhibited this degree of heart failure went on to die, while 20 percent (393/1934) of those patients who did not require an angiotensin converting enzyme inhibitor died during the period of observation (relative risk=4.5; 95 percent confidence interval, 3.6 to 5.6; P<0.001). However, patients randomized to receive captopril were significantly less likely to exhibit this form of treatment failure when compared with those on placebo [179 of 1116 (16.0 percent) on placebo versus 118 of 1115 (10.6 percent) on captopril]; the reduction in risk for requiring open-label angiotensin converting enzyme inhibition was 37 percent (95 percent confidence interval, 20 to 50 percent; P<0.001) (FIG. 2). The group randomized to captopril also exhibited a considerable reduction in the number of patients who died subsequent to going on open-label therapy with an angiotensin converting enzyme inhibitor (71 on placebo versus 39 on captopril; the reduction in risk was 47 percent; 95 percent confidence interval, 21 to 64 percent; P=0.002) (FIG. 2).

Treatment failure resulting in the need for hospitalization for the management of congestive heart failure was an even worse prognostic sign: 15 percent (346/2231) of the enrolled population manifested this degree of heart failure. Irrespective of therapy assignment, the requirement of hospitalization for the management of congestive heart failure was associated with a markedly increased risk of death: 47 percent (164/346) of those patients who exhibited this degree of heart failure went on to die while 18 percent (339/1885) of those patients who were not hospitalized for heart failure died (relative risk=6.4; 95 percent confidence interval, 5.3 to 7.8; P<0.001). Randomization to captopril therapy reduced the number of patients who required hospitalization for congestive heart failure (placebo: 17 percent, 192 of 1116 versus captopril: 14 percent, 154 of 1115; the reduction in risk for hospitalization for heart failure was 22 percent; 95 percent confidence interval, 4 to 37 percent; P=0.019). The captopril group also exhibited a substantial reduction in the number of patients who were hospitalized for congestive heart failure and who subsequently died (101 on placebo versus 64 on captopril; the reduction in risk was 38 percent; 95 percent confidence interval, 15 to 54 percent; P=0.003) (FIG. 2).

There were 303 clinical, recurrent myocardial infarctions, 170 of which occurred in the placebo group and 133 in the captopril group; the reduction in risk was 25 percent (95 percent confidence interval, 5 to 40 percent; P=0.015) (FIG. 2). The number of deaths following a recurrent myocardial infarction tended to be lower in the captopril group when compared with placebo (placebo, 80 and captopril, 56); the reduction in risk was 32 percent (95 percent confidence interval, 4 to 51 percent; P=0.029).

Figure 3:
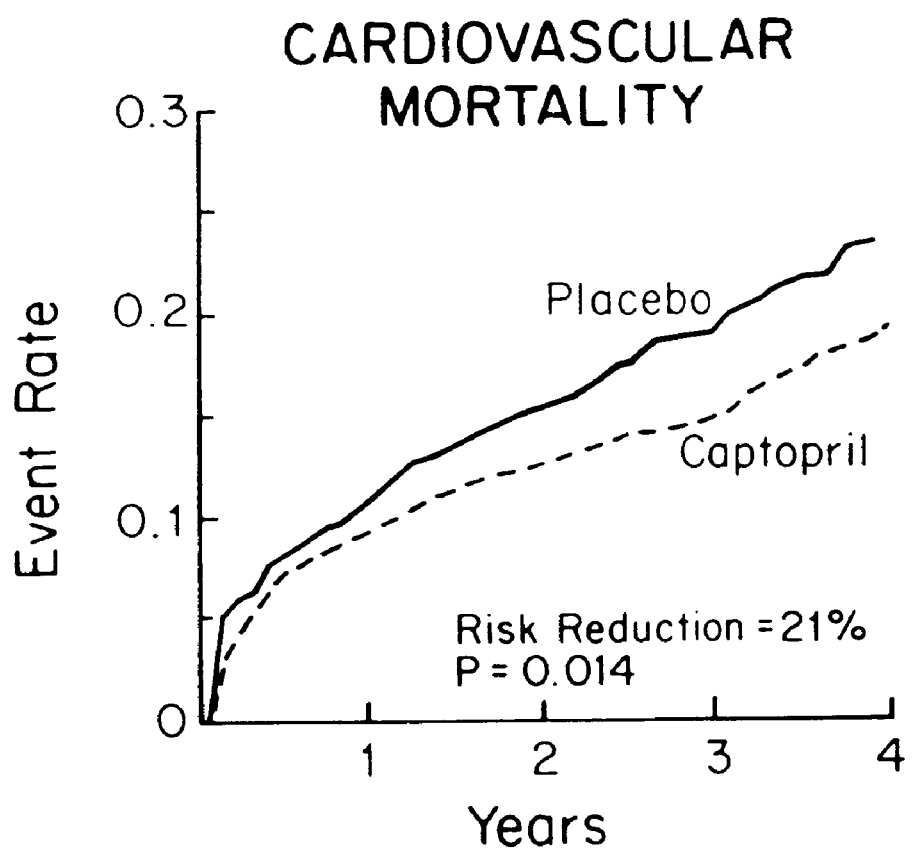
FIG. 3 is a graph depicting cardiovascular mortality for placebo treated survivors compared to captopril treated survivors.
Figure 4:
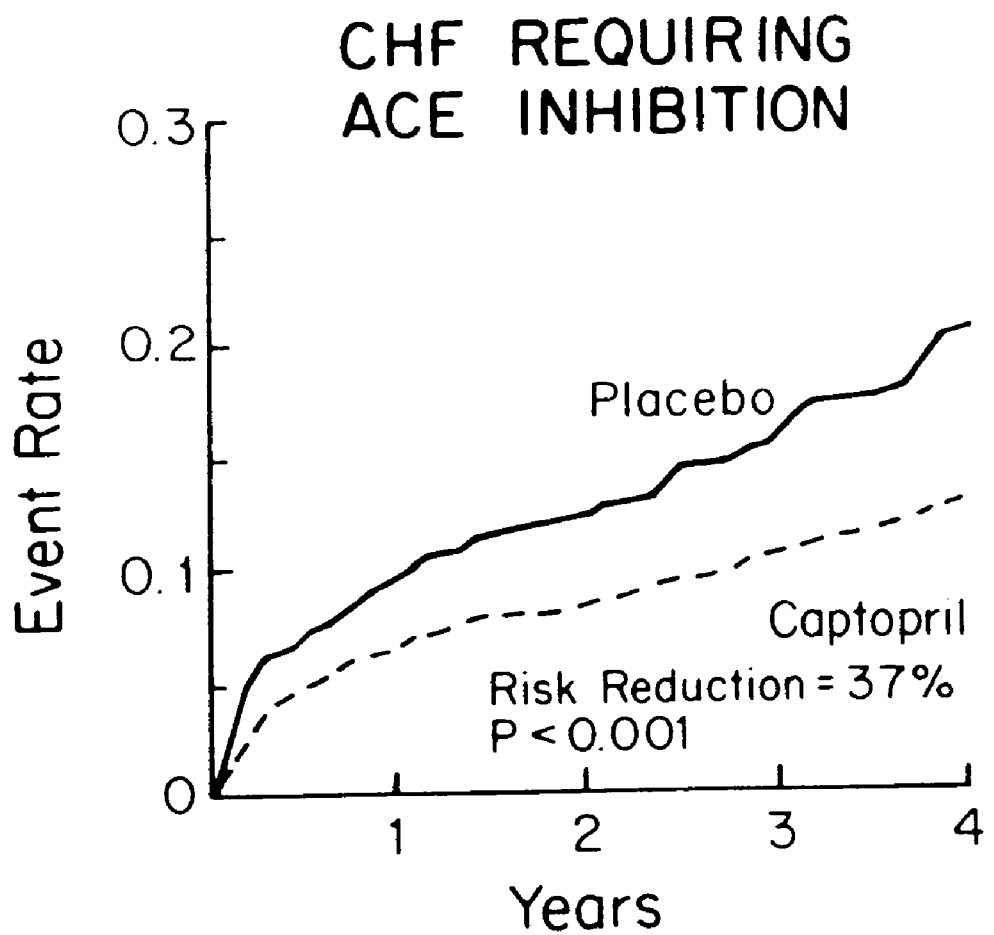
FIG. 4 is a graph depicting congestive heart failure (requiring angiotensin converting enzyme inhibition treatment) for placebo treated survivors compared to captopril treated survivors.
Figure 5:
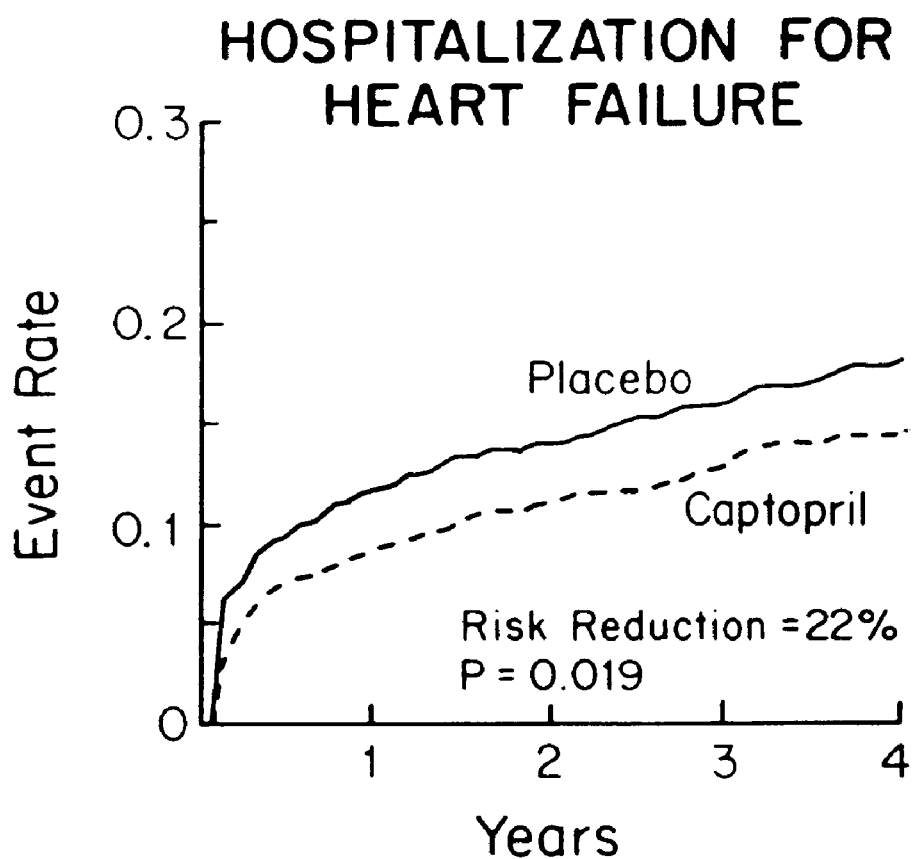
FIG. 5 is a graph depicting congestive heart failure (requiring hospitalization) for placebo treated survivors compared to captopril treated survivors.
Figure 6:
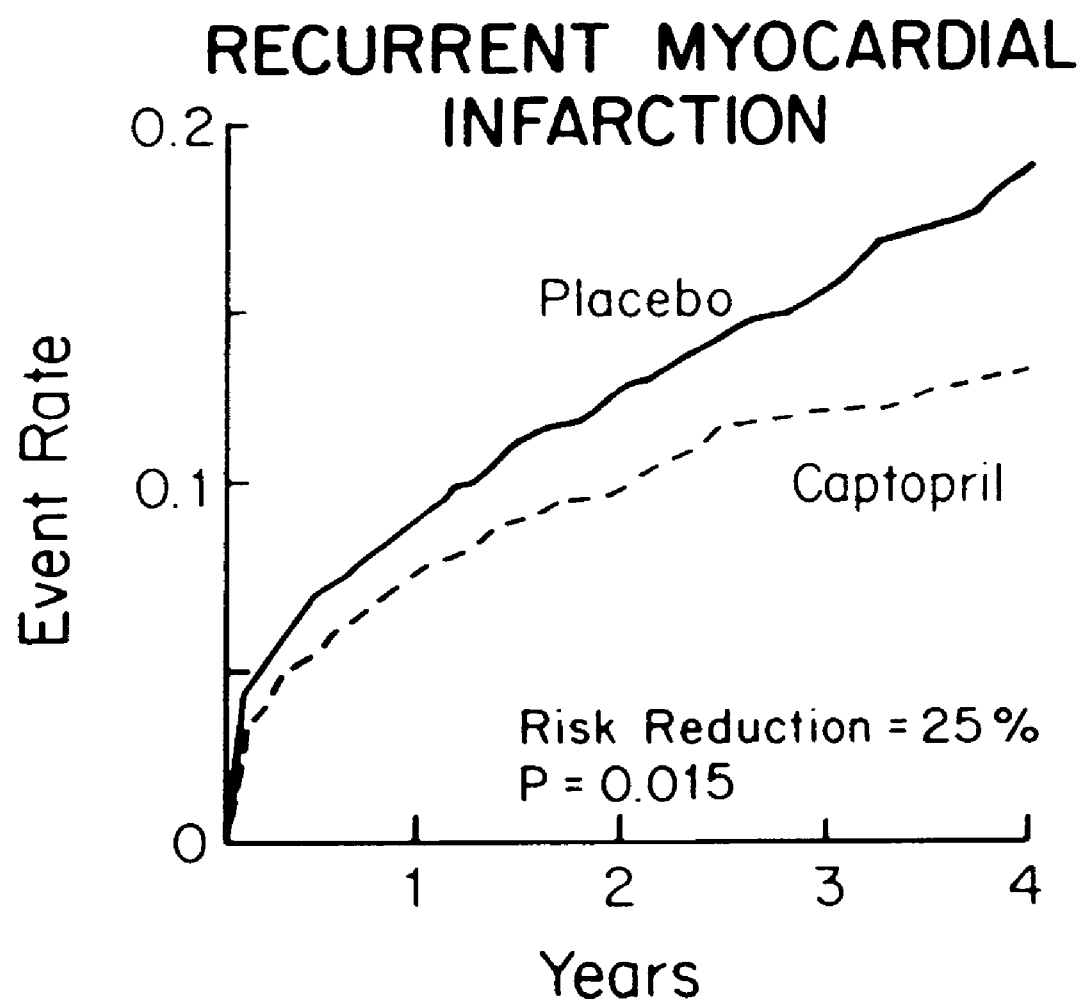
FIG. 6 is a graph depicting recurrent myocardial infarction for placebo treated survivors compared to captopril treated survivors.
Figure 7:
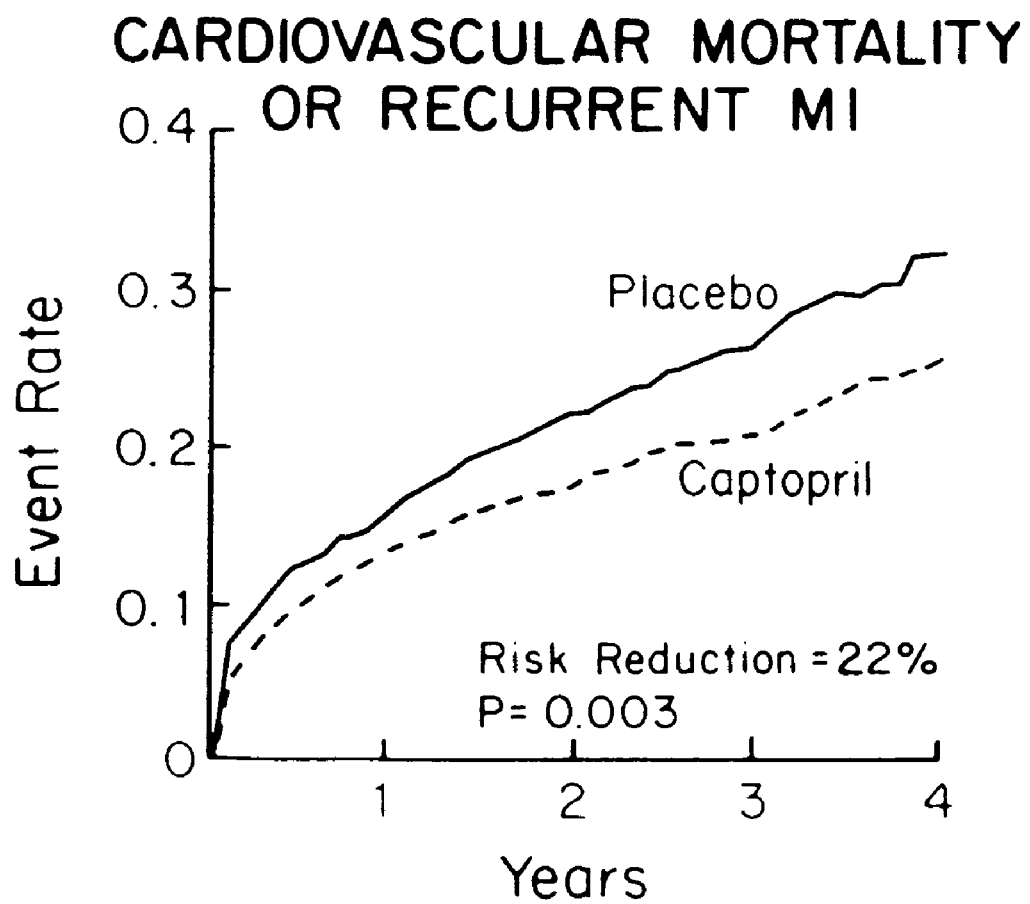
FIG. 7 is a graph depicting cardiovascular mortality plus recurrent myocardial infarction for placebo treated survivors compared to captopril treated survivors.
Figure 8:
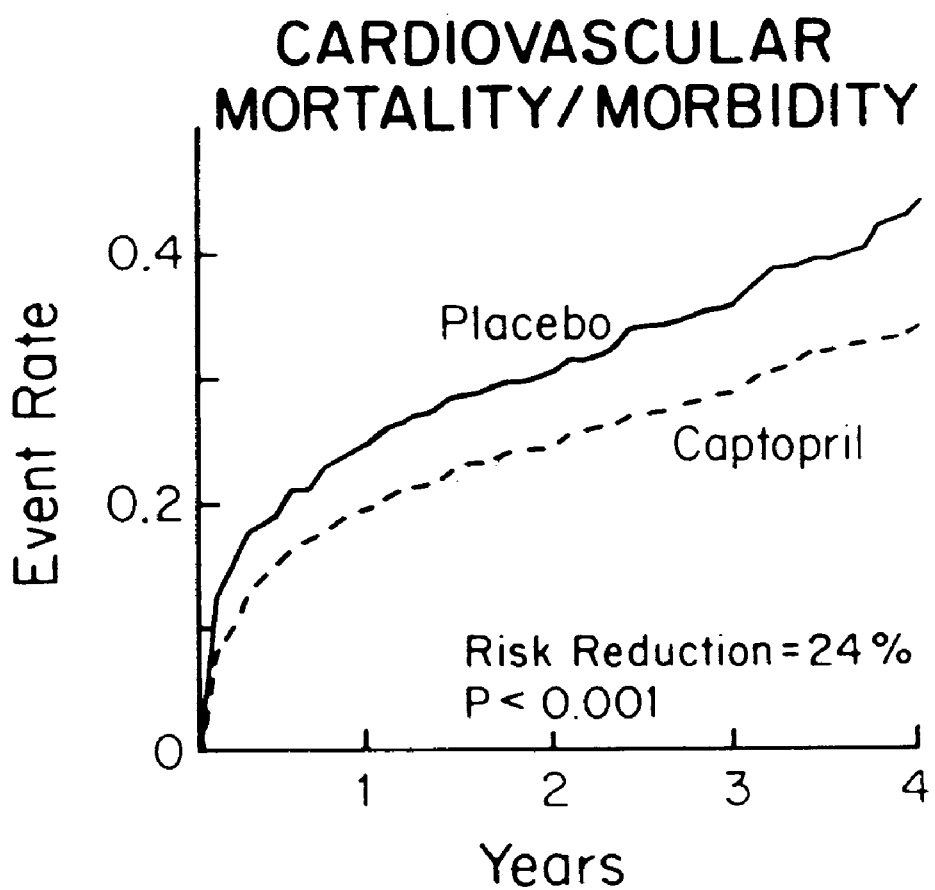
FIG. 8 is a graph depicting cardiovascular mortality plus morbidity for placebo treated survivors compared to captopril treated survivors.

FIGS. 3–8 show life table graphs which illustrate the beneficial effect of captopril therapy in reducing the incidence of the major adverse cardiovascular events. FIG. 3 shows the benefit of captopril therapy for decreasing cardiovascular mortality; FIG. 4 shows the benefit of captopril therapy for reducing the incidence of congestive heart failure requiring ACE inhibition; FIG. 5 shows the benefit of captopril therapy for decreasing the incidence of hospitalization due to heart failure; FIG. 6 shows the benefit of captopril therapy for reducing recurrent myocardial infarction; FIG. 7 shows the benefit of captopril therapy for reducing both cardiovascular mortality and recurrent MI; and FIG. 8 shows the benefit of captopril therapy for reducing both cardiovascular mortality and morbidity (severe heart failure requiring either ACE inhibitor therapy, hospitalization, or development of recurrent myocardial infarction). (For all combined analyses, only the time to first event was utilized).

The effect on all cause mortality and cardiovascular mortality and morbidity of major, prospectively specified, pre-randomization characteristics known to influence survival following myocardial infarction was as anticipated; that is, irrespective of treatment assignment, advanced age, history of prior myocardial infarction, lower left ventricular ejection fraction, and higher Killip Classification were associated with a greater incidence of adverse events. When these subgroups were analyzed, captopril therapy showed a consistent benefit, although to varying degrees, in reducing all cause mortality and cardiovascular mortality and morbidity (Table 3). Of particular note was the efficacy of captopril in Killip class I patients, i.e., those who did manifest even transient pulmonary congestion at the time of their acute myocardial infarction. Captopril also was efficacious in patients who were receiving aspirin and/or beta-blocking agents at the time of randomization, illustrating its additive value to an already proven therapy for the management of patients following a myocardial infarction. The directional benefit of captopril was uniform, for in no instance was its effect on risk reduction discordant within subgroups.

TABLE 3

Effect of Captopril on Major Clinical End points in Various Subgroups Known to Have Important Influence on Survival Following Myocardial Infarction.

| VARIABLE | PLACEBO | | CAPTOPRIL | | RISK REDUCTION (95% CI) percent | |
|---|---|---|---|---|---|---|
| | (events/number (percent) | | | | | |
| DEATH (ALL CAUSE) | | | | | | |
| Age (years): | | | | | | |
| ≦55 | 54/365 | (14.8) | 52/375 | (13.9) | 8 | (−34 to 37) |
| 56–64 | 77/352 | (21.9) | 69/356 | (19.4) | 13 | (−21 to 37) |
| >64 | 144/399 | (36.1) | 107/384 | (27.9) | 25 | (4 to 42) |
| Sex: male | 234/912 | (25.7) | 191/929 | (20.6) | 22 | (6 to 36) |
| female | 41/204 | (20.1) | 37/186 | (19.9) | 2 | (−53 to 37) |
| Prior Myocardial Infarction: | | | | | | |
| No | 144/721 | (20.0) | 115/718 | (16.0) | 22 | (0 to 39) |
| Yes | 131/395 | (33.2) | 113/397 | (28.5) | 16 | (−8 to 35) |
| EF (percent): | | | | | | |
| >32 | 77/517 | (14.9) | 75/531 | (14.1) | 6 | (−29 to 32) |
| ≦32 | 198/599 | (33.1) | 153/584 | (26.2) | 24 | (6 to 38) |
| Killip Class: | | | | | | |
| I | 140/672 | (20.8) | 109/676 | (16.1) | 25 | (4 to 42) |
| II or higher | 135/144 | (30.4) | 119/439 | (27.1) | 11 | (−14 to 31) |
| Myocardial Infarction Classification by ECG: | | | | | | |
| Anterior Q | 117/605 | (19.3) | 112/624 | (17.9) | 9 | (−19 to 29) |
| Inferior Q | 41/193 | (21.2) | 36/201 | (17.9) | 16 | (−32 to 46) |
| Both | 48/135 | (35.6) | 30/126 | (23.8) | 38 | (2 to 60) |
| Non Q | 34/110 | (30.9) | 22/106 | (20.8) | 36 | (−10 to 62) |
| Other | 35/73 | (47.9) | 28/58 | (48.3) | −2 | (−69 to 38) |
| Thrombolytic Therapy: | | | | | | |
| Yes | 58/355 | (16.3) | 48/376 | (12.8) | 22 | (−14 to 47) |
| No | 217/761 | (28.5) | 180/739 | (24.4) | 17 | (−1 to 32) |
| Beta Blocker: | | | | | | |
| Yes | 76/398 | (19.1) | 52/391 | (13.3) | 33 | (4 to 53) |
| No | 199/718 | (27.7) | 176/724 | (24.3) | 14 | (−5 to 30) |
| Asprin | | | | | | |
| Yes | 140/653 | (21.4) | 109/657 | (16.6) | 24 | (2 to 41) |
| No | 135/463 | (29.2) | 119/458 | (26.0) | 14 | (−10 to 33) |
| TOTAL | 275/1116 | (24.6) | 228/1115 | (20.4) | 19 | (3 to 32) |
| CV DEATH OR MORBIDITY* | | | | | | |
| Age (years): | | | | | | |
| ≦55 | 104/365 | (28.5) | 97/375 | (25.9) | 10 | (−18 to 32) |
| 56–64 | 152/352 | (43.2) | 112/356 | (31.5) | 34 | (16 to 48) |
| >64 | 192/399 | (48.1) | 150/384 | (39.1) | 23 | (5 to 38) |
| Sex: male | 367/912 | (40.2) | 288/929 | (31.0) | 28 | (16 to 38) |
| female | 81/204 | (39.7) | 71/186 | (38.2) | 4 | (−32 to 30) |
| Prior Myocardial Infarction: | | | | | | |
| No | 228/721 | (31.6) | 186/718 | (25.9) | 21 | (4 to 35) |
| Yes | 220/395 | (55.7) | 173/397 | (43.6) | 29 | (13 to 42) |
| EF (percent): | | | | | | |
| >32 | 155/517 | (30.0) | 124/531 | (23.4) | 27 | (7 to 42) |
| ≦32 | 293/599 | (48.9) | 235/584 | (40.2) | 22 | (7 to 34) |
| Killip Class: | | | | | | |

TABLE 3-continued

Effect of Captopril on Major Clinical End points in Various Subgroups
Known to Have Important Influence on Survival Following Myocardial Infarction.

| VARIABLE | PLACEBO | | CAPTOPRIL | | RISK REDUCTION (95% CI) percent | |
|---|---|---|---|---|---|---|
| | (events/number (percent)) | | | | | |
| I | 225/672 | (33.5) | 179/676 | (26.5) | 25 | (8 to 38) |
| II or higher | 223/444 | (50.2) | 180/439 | (41.0) | 23 | (7 to 37) |
| Myocardial Infarction Classification by ECG: | | | | | | |
| Anterior Q | 198/605 | (32.7) | 177/624 | (28.4) | 16 | (−3 to 31) |
| Inferior Q | 76/193 | (39.4) | 61/201 | (30.3) | 28 | (−1 to 49) |
| Both | 75/135 | (55.6) | 50/126 | (39.7) | 35 | (7 to 55) |
| Non Q | 51/110 | (46.4) | 38/106 | (35.8) | 31 | (−5 to 55) |
| Other | 48/73 | (65.8) | 33/58 | (56.9) | 20 | (−25 to 49) |
| Thrombolytic Therapy: | | | | | | |
| Yes | 117/355 | (33.0) | 99/376 | (26.3) | 23 | (−1 to 41) |
| No | 331/761 | (43.5) | 260/739 | (35.2) | 24 | (11 to 36) |
| Beta Blocker: | | | | | | |
| Yes | 132/398 | (33.2) | 103/391 | (26.3) | 26 | (4 to 43) |
| No | 316/718 | (44.0) | 256/724 | (35.4) | 23 | (10 to 35) |
| Asprin | | | | | | |
| Yes | 239/653 | (36.6) | 203/657 | (30.9) | 20 | (3 to 33) |
| No | 209/463 | (45.1) | 156/458 | (34.1) | 29 | (13 to 43) |
| TOTAL | 448/1116 | (40.1) | 359/1115 | (32.2) | 24 | (13 to 34) |

*CV Death or Morbidity designates either a death classified as having a cardiovascular origin or the development of congestive heart failure requiring the use of open-label angiotensin converting enzyme inhibitor for management of congestive heart failure, the development of heart failure requiring a hospital admission for management, or a recurrent myocardial infarction. With this analysis, any patient can only experience one of these major fatal or non-fatal cardiovascular events. The percentage risk reduction and 95% confidence interval (CI) are indicated in brackets.
EF indicates radionuclide left ventricular ejection fraction at base-line.
ECG indicates electrocardiogram.

Adherence and Adverse Study Drug Experience

The number of patients taking their assigned study medication at one-year was similar for the placebo (808/985, 82 percent) and captopril (787/1001, 79 percent) groups (P=NS). At the last study visit, 73 percent (612/841) of the patients in the placebo group and 70 percent (619/887) of the patients in the captopril group were still on study drug (P=NS). Of those taking their assigned study medication at the last visit, 90 percent (549/612) of placebo and 79 percent (486/619) of captopril patients achieved the target dose of 150 mg per day.

Captopril-treated patients registered significantly more (Z>1.96, uncorrected; excess over placebo) complaints of dizziness (5.5 percent); taste alteration (2.5 percent); diarrhea (2.1 percent); and cough (6.2 percent). The number of patients who discontinued study medication at the time of these adverse events in the placebo and captopril groups, respectively, was: 25 and 32 for dizziness (P=NS); 5 and 9 for taste alteration (P=NS); 9 and 27 for cough (P=0.003); and none for diarrhea. A minor, but statistically significant difference in the serum creatinine level was detected between the treatment groups during the follow-up period (two-year values for placebo and captopril, respectively: 106 versus 110 $\mu$mol/liter, or 1.20 versus 1.24 mg/dl; P=0.014).

DISCUSSION

The randomization window of 3 to 16 days was chosen to allow the treating physician time to formulate an individualized plan for the management of coronary artery disease. Indeed, of the total study population, 55 percent had a catheterization and 26 percent had a revascularization procedure (9 percent had coronary artery bypass surgery and 17 percent had percutaneous transluminal coronary angioplasty) performed following the infarction but prior to enrollment. Although this randomization period precluded the opportunity for captopril to influence the early (<72 hours) changes in left ventricular topography that may occur following myocardial infarction (22), the long-term efficacy of captopril therapy in reducing adverse clinical events did not appear to be influenced by the differences in the time to initiation of therapy (Table 3).

The selection of patients with objective evidence of left ventricular dysfunction (ejection fraction$\leq$40 percent) was based on the finding in previous clinical studies (17,18) that captopril attenuated ventricular dilatation in this patient population. The exclusion from this trial of patients with symptomatic heart failure who required vasodilators was based on the demonstrated efficacy of this therapy for the treatment of heart failure (23,24,25). In the present study the efficacy of captopril therapy in reducing death and major adverse cardiovascular events appeared to increase during follow-up (FIGS. 1 and 3–8), underscoring the value of this agent as preventive therapy in patients with left ventricular dysfunction but without overt heart failure following a myocardial infarction. The present study demonstrates that the long-term administration of captopril to survivors of a myocardial infarction, a high risk population, resulted in a reduction not only in the manifestation of heart failure, but also in the number of subsequent fatal events.

Although not wishing to be bound by any particular theory, the favorable effects of captopril therapy may be explained by its attenuation of ventricular remodeling and/or by its direct inhibition of the proposed deleterious effects of neurohumoral activation (26). These purported mechanisms by which captopril might exert its beneficial effects are not mutually exclusive. Indeed, the combination of ventricular enlargement and elevated plasma levels of neurohormones at base line was associated with a greater risk of death than that for the presence of these adverse prognostic indicators alone (27). These same actions of captopril on ventricular remodeling and neurohumoral profile may also be operative in reducing the incidence of recurrent myocardial infarction.

The foregoing description of the invention and the example demonstrating the application of the invention are but illustrative. Other variations and equivalents will be apparent to those of ordinary skill in the art. Therefore, the present invention is to be considered limited only by the appended claims.

REFERENCES

1. Kannel W B, Sorlie P, McNamara P M Prognosis after initial myocardial infarction: The Framingham Study. Am J Cardiol 1979; 44:53–9.

2. The Multicenter Postinfarction Research Group. Risk stratification and survival after myocardial infarction. N Engl J Med 1983; 309:331–6.

3. Stadius M L, Davis K, Maynard C, Ritchie J L, Kennedy J W. Risk stratification for 1 year survival based on characteristics identified in the early hours of acute myocardial infarction. The Western Washington Intracoronary Streptokinase Trial. Circulation 1986; 74:703–11.

4. Hammermeister K E, DeRouen T A, Dodge H T. Variables predictive of survival in patients with coronary disease: selection by univariate and multivariate analyses from the clinical, electrocardiographic, exercise, arteriographic, and quantitative angiographic evaluations. Circulation 1979; 59:421–30.

5. White H D, Norris R M, Brown M A, Brandt P W T, Whitlock R M L, Wild C J. Left ventricular end-systolic volume as the major determinant of survival after recover from myocardial infarction. Circulation 1987; 76:44–51.

6. Fletcher P J, Pfeffer J M, Pfeffer M A, Braunwald E. Left ventricular diastolic pressure-volume relations in rats with healed myocardial infarction: effects on systolic function. Circ Res 1981; 49:618–26.

7. Pfeffer P J, Pfeffer M A, Fletcher P J, Braunwald E. Progressive ventricular remodeling in rat with myocardial infarction. Am J Physiol 1991; 260 (HCP 29):H1406–14.

8. Eaton L W, Weiss J L, Bulkley B H, Garrison J B, Weisfeldt M L. Regional cardiac dilatation after acute myocardial infarction: recognition by two-dimensional echocardiography. N Engl J Med 1979; 300:57–62.

9. McKay R G, Pfeffer M A, Pasternak R C, et al. Left ventricular remodeling after myocardial infarction: a corollary to infarct expansion. Circulation 1986; 74:693–702.

10. Gaudron P, Eilles C, Ertl G, Kochsiek K. Early remodeling of the left ventricle in patients with myocardial infarction. Europ Heart J 1990; 11 (Suppl B):139–46.

11. Pfeffer M A, Braunwald E. Ventricular remodeling after myocardial infarction. Circulation 1990; 81:1161–72.

12. Pfeffer J M, Pfeffer M A, Braunwald E. Influence of chronic captopril therapy on the infarcted left ventricle of the rat. Circ Res 1985; 57:84–95.

13. Pfeffer M A, Pfeffer J M, Steinberg C, Finn P. Survival after an experimental myocardial infarction: beneficial effects of long-term therapy with captopril. Circulation 1985; 72:406–12.

14. Packer M, et al. Effect of oral milirone on mortality in sever chronic heart failure. N Engl J Med 1991; 325:1468–1475.

15. The Multicenter European Research Trial with Cilazapril After Angioplasty to Prevent Transluminal Coronary Obstruction and Restenosis (MERCATOR) Study Group. Does the New Angiotensin Converting Enzyme Inhibitor Cilazapril Prevent Restenosis After Percutaneous Transluminal Coronary Angioplasty? Circulation 1992; 86:1, 100–110.

16. Jeremy R W, Allman K C, Bautovitch G, Harris P J. Patterns of left ventricular dilation during the six months after myocardial infarction. J Am Coll Cardiol 1989; 13:304–10.

17. Pfeffer M A, Lamas G A, Vaughan D E, Parisi A F, Braunwald E. Effect of captopril on progressive ventricular dilation after anterior myocardial infarction. N Engl J Med 1988; 319:80–6.

18. Sharpe N, Smith H, Murphy J, Hannan S. Treatment of patients with symptomless left ventricular dysfunction after myocardial infarction. Lancet 1988; 1:255–9.

19. Swedberg K. Lack of beneficial effects on mortality by early intervention with enalapril in acute myocardial infarction. Circulation 1991; supplement II; 84, II-366.

20. Moye L A, Pfeffer M A, Braunwald E, for the SAVE Investigators. Rationale, design and baseline characteristics of the survival and ventricular enlargement trial. Am J Cardiol 1991; 68:70D–79D.

21. Moye L A, Davis B R, Hawkins C M. Analysis of a clinical trial involving a combined mortality and adherence dependent interval censored endpoint. Statistics in Medicine. January 1992. (Accepted)

22. Nabel E G, Topol E J, Galeana A, et al. A randomized placebo-controlled trial of combined early intravenous captopril and recombinant tissue-type plasminogen activator therapy in acute myocardial infarction. J Am Coll Cardiol 1991; 17:467–73.

23. Consensus Trial Study Group. Effects of enalapril on mortality in severe congestive heart failure. Results of the Cooperative North Scandinavian Enalapril Survival Study (CONSENSUS). N Engl J Med 1987; 316:1429–35.

24. Cohn J N, Archibald D G, Ziesche S, et al. Effect of vasodilator therapy on mortality in chronic congestive heart failure. Results of a Veterans Administration Cooperative Study. N Engl J Med 1986; 314:1547–52.

25. The SOLVD Investigators. Effect of enalapril on survival in patients with reduced left ventricular ejection fractions and congestive heart failure. N Engl J Med 1991; 325:293–302.

26. Packer M, Lee W H, Kessler P D, Gottlieb S S, Bernstein J L, Kukin M L. Role of neurohormonal mechanisms in determining survival in patients with severe chronic heart failure. Circulation 1987; 75 (Suppl IV):IV-80–IV-92.

27. Sussex B A, Arnold J M O, Parker J O, et al. Independent and interactive prognostic information of neurohormones and echocardiogram in high risk post-MI patients. J. Am. Coll. Cardiol. 1992; 19:205A (Abstract).

What we claim is:

1. A method for treating a human survivor of a myocardial infarction who is free of hypertension and congestive heart failure and is otherwise free of indications for angiotensin II inhibition treatment to prevent repeat myocardial infarction and to increase the likelihood of survival following the myocardial infarction comprising:

administering to the human survivor who is free of hypertension and congestive heart failure and is otherwise free of indications for angiotensin II inhibition treatment a therapeutically effective amount of an angiotensin II inhibitors wherein the human survivor has a left ventricular ejection fraction of less than or equal to 40% after the myocardial infarction.

2. A method for treating a human survivor of a myocardial infarction as claimed in claim 1 wherein the inhibitor is an angiotensin II antagonist.

3. A method as claimed in claim 2 wherein the angiotensin II antagonist is Losartan (2-N-butyl-4-chloro-5-hydoxmethyl-1-[(2'-1H-tetrazol-5-yl)biphenyl-4-yl methyl] imadazole.

4. A method as claimed in claim 1, wherein the angiotensin II inhibitor is a peptide.

5. A method as claimed in claim 1, wherein the angiotensin II inhibitor is administered for an extended period of time.

6. A method as claimed in claim 1, wherein the angiotensin II inhibitor is administered to the human survivor within 16 days of the myocardial infarction.

7. A method as claimed in claim 1, wherein the angiotensin II inhibitor is administered to the human survivor only after three days have passed since the myocardial infarction.

8. A method as claimed in claim 1, wherein the angiotensin II inhibitor is administered to the human survivor within 16 days of the myocardial infarction, but only after 3 days have passed since the myocardial infarction, and wherein the angiotensin II inhibitor is administered for an extended period of time to the survivor.

9. A method as claimed in claim 1, wherein the angiotensin II inhibitor is administered at the maximum dose tolerable.

10. A method as claimed in any one of claims 5, 6, 7, 8 and 9, wherein the angiotensin II inhibitor is an angiotensin II antagonist.

11. A method as claimed in claim 10, wherein the angiotensin II antagonist is a peptide.

* * * * *